United States Patent
Jarry et al.

(10) Patent No.: US 8,851,883 B2
(45) Date of Patent: Oct. 7, 2014

(54) PREHEATING OF FUEL AND OXIDANT OF OXY-BURNERS, USING COMBUSTION AIR PREHEATING INSTALLATIONS

(75) Inventors: Luc Jarry, Meudon (FR); Bertrand Leroux, Linas (FR)

(73) Assignee: L'Air Liquide, Societe Anonyme pour l'Etude et l'Exploitation des Procedes Georges Claude, Paris (FR)

( * ) Notice: Subject to any disclaimer, the term of this patent is extended or adjusted under 35 U.S.C. 154(b) by 762 days.

(21) Appl. No.: 12/064,654

(22) PCT Filed: Aug. 17, 2006

(86) PCT No.: PCT/FR2006/050803
§ 371 (c)(1),
(2), (4) Date: May 15, 2012

(87) PCT Pub. No.: WO2007/023238
PCT Pub. Date: Mar. 1, 2007

(65) Prior Publication Data
US 2010/0291493 A1    Nov. 18, 2010

(30) Foreign Application Priority Data

Aug. 25, 2005  (FR) .................................. 05 52561

(51) Int. Cl.
*F23N 1/02* (2006.01)
*F23C 15/00* (2006.01)
*F23D 11/44* (2006.01)
*F27B 3/00* (2006.01)
*C21D 1/767* (2006.01)
*C10B 21/20* (2006.01)
*F24H 3/00* (2006.01)

(52) U.S. Cl.
USPC ................. 431/12; 431/1; 431/207; 431/215; 431/239; 431/245; 431/246; 432/13; 432/21; 432/31; 126/99 R

(58) Field of Classification Search
USPC ............... 431/12, 1, 239, 215, 207, 245, 246; 432/13, 21, 31; 126/15 A, 99 R
See application file for complete search history.

(56) References Cited

U.S. PATENT DOCUMENTS 5,147,438 A * 9/1992 Castelain et al. ............ 65/134.4
5,921,771 A * 7/1999 Kobayashi .................... 432/181
(Continued)

FOREIGN PATENT DOCUMENTS

| EP | 0 440 085 | 8/1991 |
|---|---|---|
| EP | 0 567 131 | 10/1993 |
| EP | 0 808 806 | 11/1997 |
| EP | 1 136 451 | 9/2001 |

OTHER PUBLICATIONS

International Search Report for PCT/FR2007/050803, mailed Jan. 25, 2007.

(Continued)

*Primary Examiner* — Kenneth Rinehart
*Assistant Examiner* — William Corboy
(74) *Attorney, Agent, or Firm* — Christopher J. Cronin

(57) ABSTRACT

The invention relates to a combustion method which is performed in a furnace that is equipped with energy recovery means and burners, whereby the heat from the combustion fumes is recovered by energy recovery means and said recovered heat is used in order to heat the air. According to the invention, at least part of the burners performs the combustion of an oxygen-rich comburent and a fuel and at least part of the air heated by the energy recovery means is used to heat the oxygen-rich comburent and/or fuel for the burners.

6 Claims, 3 Drawing Sheets

(56) References Cited

U.S. PATENT DOCUMENTS

Figure 1:
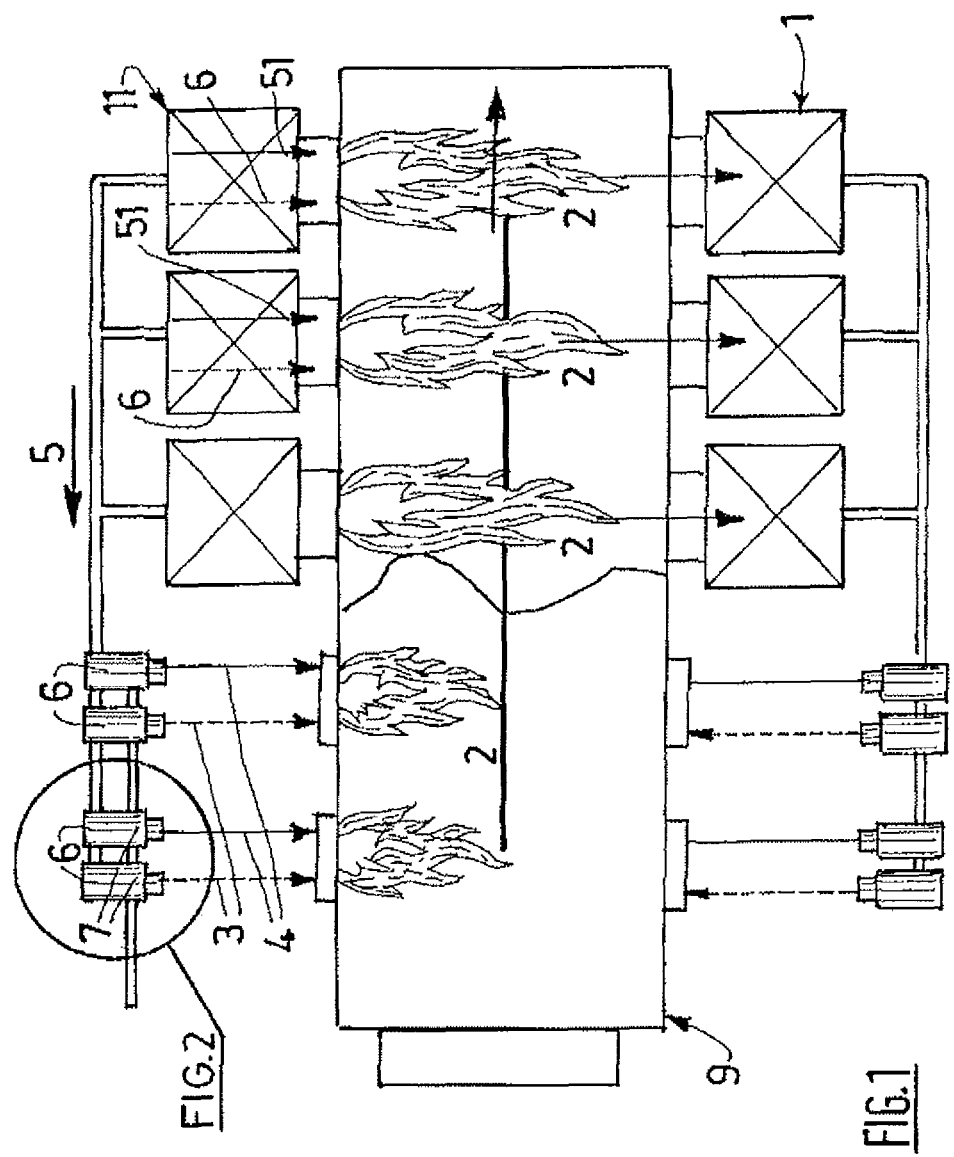

| | | | |
|---|---|---|---|
| 6,041,622 A * | 3/2000 | Duchateau et al. | 65/134.4 |
| 6,126,440 A * | 10/2000 | Argent et al. | 432/181 |
| 6,217,681 B1 | 4/2001 | Bazarian et al. | |
| 6,250,916 B1 * | 6/2001 | Philippe et al. | 432/29 |
| 6,519,973 B1 * | 2/2003 | Hoke et al. | 65/134.4 |

OTHER PUBLICATIONS

McMahon, A., et al., "A partial conversion of a gas-air fired television furnace to oxy-fuel combustion," J. of Non-Crystalline Solids, North-Holland Physics Publ., Amsterdam, NL, vol. 177, Nov. 1994, pp. 462-435.

* cited by examiner

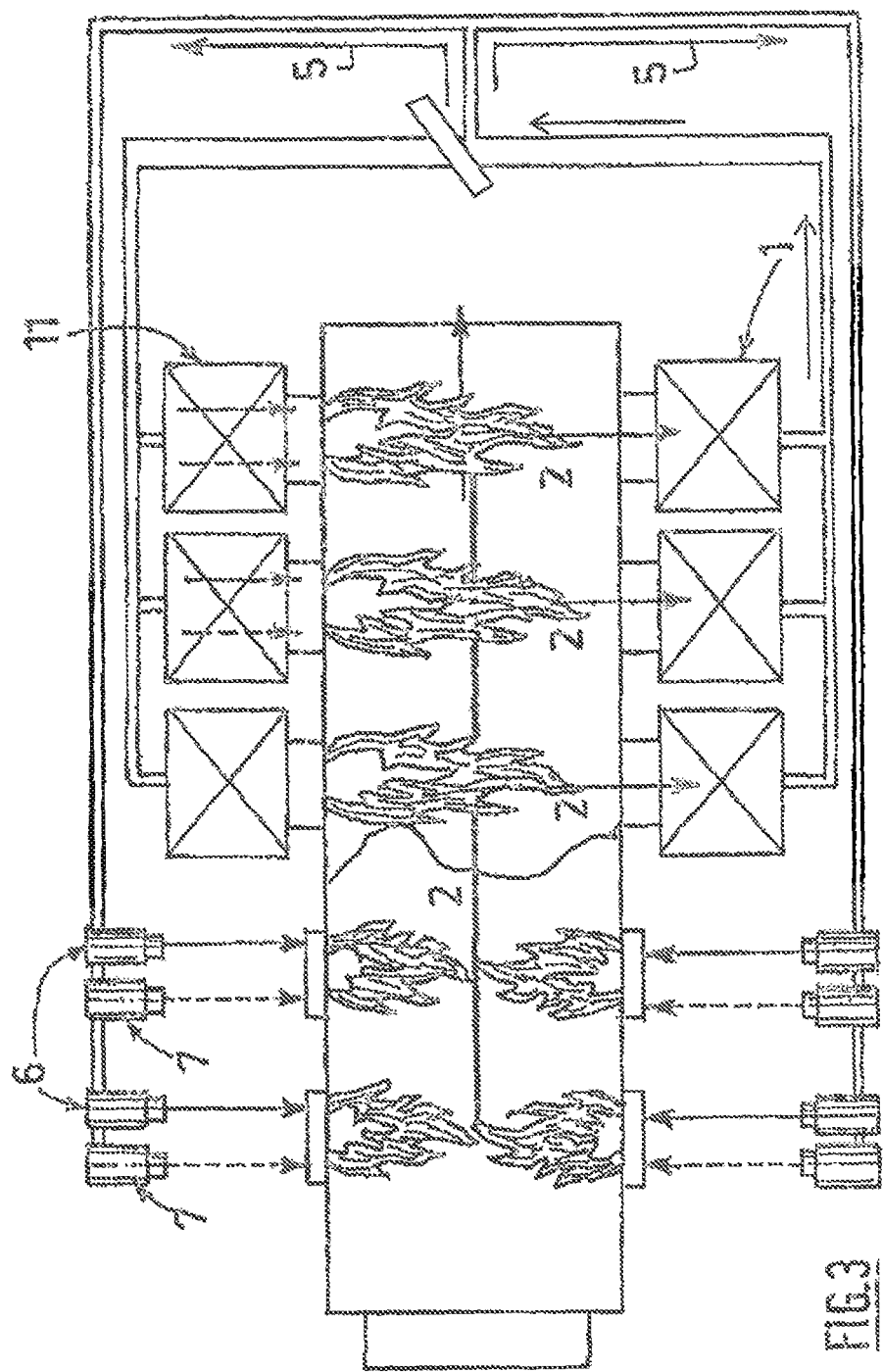

PREHEATING OF FUEL AND OXIDANT OF OXY-BURNERS, USING COMBUSTION AIR PREHEATING INSTALLATIONS

This application is a 371 of International PCT Application PCT/FR2006/050803, filed Aug. 17, 2007.

The present invention relates to the installation of an oxy-combustion method with oxygen and/or fuel preheating in a furnace equipped with means for employing aero-combustion with air preheating.

Regenerator furnaces are furnaces equipped with stacks of refractories on their sidewalls. These refractories are heat exchangers enabling heat to be recovered from combustion flue gases leaving the sidewalls of the furnace and of transferring this heat to cold air provided to the furnace. The refractories of regenerators are heated to very high temperatures (of the order of 1300 to 1500° C.) by the combustion flue gases. In practice, the combustion flue gases leaving through a sidewall of the furnace are brought into contact with the refractories from their upper part to their lower part over a cycle generally of approximately 20 minutes. During the following cycle, cold combustion air intended to feed the burners of the furnace is brought into contact with the refractories from their lower part to their upper part so as to extract the heat therefrom. The combustion air is then heated to a temperature generally of the order of 1100 to 1300° before being introduced into the combustion chamber of the furnace. The streams of combustion flue gases and combustion air are reversed at each cycle so that each regenerator face can be heated alternately and used for preheating the combustion air. Preheating combustion air makes combustion with air possible with a high energy yield. For furnaces with recuperators, the combustion air is heated continuously by metal exchangers fed with combustion flue gases.

Many furnaces now operate with oxy-combustion, which means that combustion is no longer carried out between the fuel and air (aero-combustion) but between fuel and an oxidant having an oxygen concentration higher than air. It generally consists of air enriched with oxygen or of pure oxygen. Preheating oxygen and fuel with flue gases from combustion products makes it possible to recover part of the energy contained therein and to improve the energy efficiency of this type of combustion. The energy contained in the flue gases from combustion products leaving a glass melting furnace equipped with oxy-fuel flames is of the order of 30% of the power consumed.

Oxy-combustion is easily implemented when new furnaces are constructed. On the other hand, it is more difficult, for economic reasons, to use only oxy-combustion in regenerator furnaces initially provided for combustion with air. One of the reasons is that it is necessary to remove regenerators, modify the dimensions of the furnace and reconstruct the evacuation of combustion flue gases. Indeed, in oxy-combustion, the volume of combustion flue gases is 4 to 5 times lower than that of combustion with air.

The object of the present invention is to provide a combustion method enabling oxy-combustion to be at least partially employed in a furnace equipped with regenerators or recuperators recovering heat from combustion flue gases.

Another object is to employ this oxy-combustion method starting with the installation of an already existing aero-combustion furnace.

Another object is to provide an oxy-combustion method that can be adapted to a furnace with regenerators or recuperators designed for combustion with air.

With this objective, the invention relates to a combustion method in a furnace equipped with means for recovering energy from combustion flue gases and burners, wherein heat from combustion flue gases is recovered by energy recovery means and this heat recovered by energy recovery means is used to heat air, and wherein:

at least part of the burners employ the combustion of a fuel and an oxygen-rich oxidant, and at least part of the air heated by energy recovery means is used to preheat the fuel and/or the oxygen-rich oxidant of the burners.

The invention therefore relates to the application of a combustion method in a furnace equipped with energy recovery means, such as regenerators or recuperators, designed for recovering energy contained in combustion flue gases. The combustion employed in the furnace is, at least partially, oxy-combustion, namely combustion of a fuel and an oxygen-rich oxidant. Preferably, at least 10%, and even more preferably 20%, of the combustion power is produced by burners employing combustion of a fuel and an oxygen-rich oxidant. "Oxygen-rich oxidant" is understood to mean a oxidant having an oxygen concentration greater than 90% by volume. Oxygen produced by a VSA (Vacuum Swing Adsorption) method is particularly suitable. According to the method of the invention, the energy recovery means are used to heat cold air, namely ambient air, by bringing thereto energy recovered from all the combustion flue gases, derived both from oxy-combustion and aero-combustion, if aero-burners are used (aero-burners are understood to mean burners in which the oxidant is air). In the prior art, this energy recovered from flue gases was only intended for preheating combustion air, namely air mixed directly with fuel in the burner. On the contrary, in the present invention, at least part of the energy contained in this air heated by means for recovering energy from combustion flue gases is directed towards the means feeding fuel and oxygen-rich oxidant of oxy-burners so as to preheat this fuel and this oxidant (oxy-burners are understood to mean burners for which the oxidant is oxygen-rich). Preheating may be carried out by any means for exchanging heat between hot air and fuel or oxidant.

It has been noted that the energy of flue gases coming from oxy-combustion can only be recovered by heating air intended for combustion in air-fuel burners if such burners are present with oxy-fuel burners. Indeed, the air flow is controlled and limited by the power and air/fuel combustion ratio of the aero-combustion installed. Similarly, the preheating temperature of combustion air is limited by the strength of refractories or other materials of the system for recovering energy from the flue gases. Thus, oxy-combustion produces an excess of energy in the flue gases and this supplementary energy contained in the oxy-combustion flue gases and evacuated by the energy recovery means of the furnace, may be recovered after preheating air of which part (or even all in the case of a furnace heated solely by oxy-burners) will be directed towards the means for preheating the fuel and oxygen-rich oxidant of oxy-burners.

When cold air is heated, air is brought to a maximum preheating temperature for a volume suited to the requirements of aero-combustion and for preheating oxygen and/or fuel of oxy-combustion. At least part of the air heated by the energy recovery means is directed towards installations for preheating the fuel and/or oxygen-rich oxidant of burners by means of a direct or indirect heat exchanger. "Indirect heat exchanger" is understood to mean a heat exchanger using an inert gas to transfer heat from hot air to the fuel and/or to the oxygen-rich oxidant. The heat of the hot air is first of all transferred to the inert gas, which then transfers its heat to the fuel and/or to the oxygen-rich oxidant. As inert gas, use may be made of nitrogen or argon for example.

The invention may be implemented when all the burners employ the combustion of a fuel and an oxygen-rich oxidant. In this case, all the air preheated by the energy recovery means is intended for exchanging heat with the fuel and/or the oxygen-rich oxidant. The invention is particularly suitable for combustion employed in a glass melting furnace.

The invention also relates to a method for converting a furnace equipped with:
- burners employing the combustion of a fuel and air;
- energy recovery means wherein the heat of combustion flue gases is recovered in order to heat the air; and
- means for feeding the burners with heated air, in a furnace employing oxy-combustion, in which:
- the air supply of at least part of the burners is replaced by a supply of oxygen-rich oxidant; and
- at least part of the air heated by the energy recovery means is used to preheat the fuel and/or the oxidant for the burners.

This conversion method has the advantage of enabling a furnace functioning with aero-combustion to be changed over to partial or total functioning in oxy-combustion while preserving the structures of the existing furnace and by using systems for recovering energy from the flue gases in order to preheat oxygen and/or fuel for oxy-combustion in order to increase the energy efficiency of the installation. It is thus possible to employ the oxy-combustion method and to profit from its advantages (higher combustion temperature and lower energy loss in the flue gases, reduction in NO and dust) without having to fundamentally redesign the furnace, particularly as regards the evacuation of flue gases, and consequently without making a large investment.

By only partially converting the oxy-combustion furnace and by using existing regenerators for preheating the oxygen and/or fuel, part of the structures of the furnace is preserved and modifications are limited to providing a system for evacuating flue gases.

FIG. 1 illustrates the method of the invention. The furnace 9 is fitted:
- upstream, with oxy-burners fed with fuel 4 and oxygen-rich oxidant 3;
- downstream, with burners fed with fuel 6 and heated air 51; and
- regenerators 1 that are either fed with hot flue gases 2 from the furnace (regenerators 1), or that return hot air 5, 51 (regenerators 11). Hot air 5 delivered by the regenerators 11 is either used as combustion air 51 in air burners or is used for preheating the fuel 4 and the oxygen-rich oxidant 3 of oxy-burners by means of heat exchangers 6, 7. In this configuration, hot air 5 coming from the regenerators 11 placed on the same side as the furnace 9 enable only air-fuel and oxy-fuel burners respectively to be supplied and preheated that are placed on their same side of the furnace, burners placed on the other side of the furnace not functioning.

Figure 2:
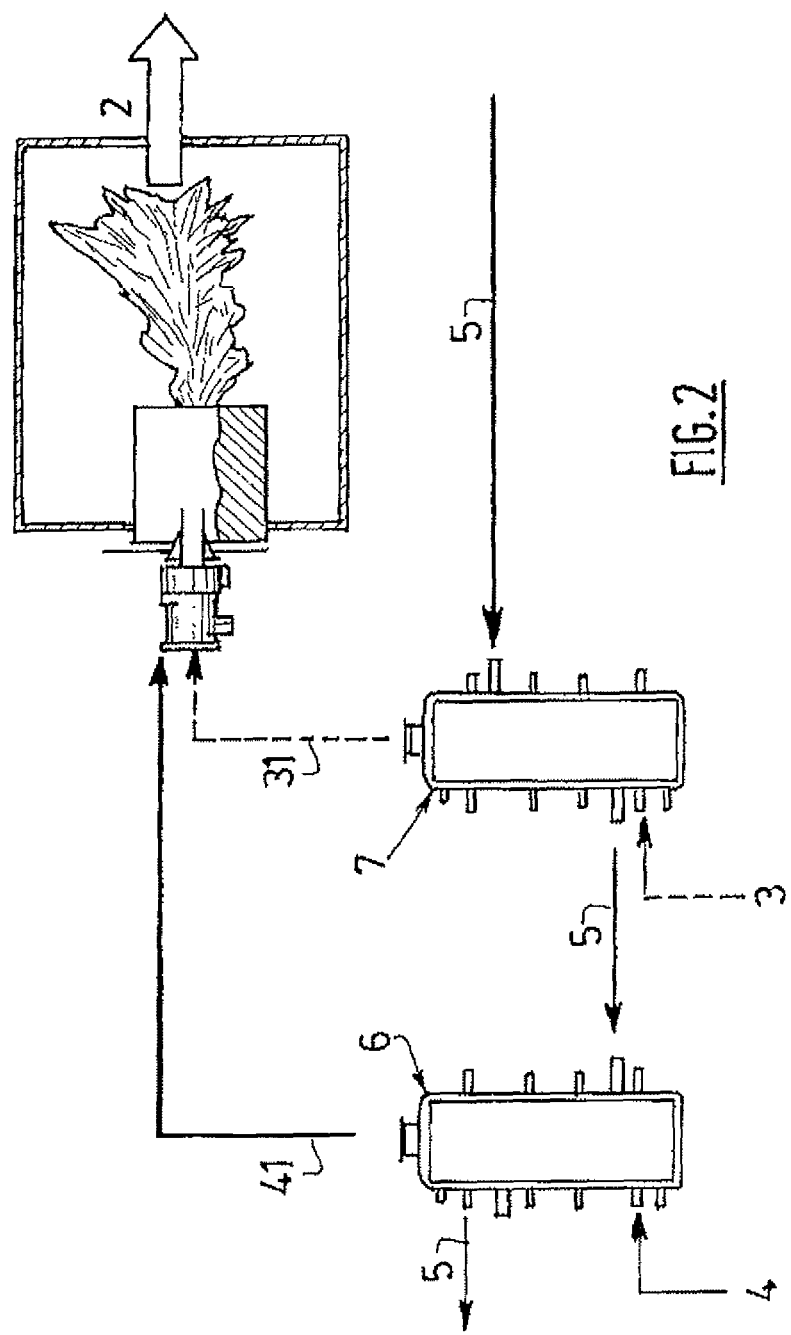

FIG. 2 illustrates the preheating of reactants: the hot air 5 coming from the regenerators 11 is introduced successively into a heat exchanger 7 in order to heat the oxygen-rich oxidant 3, and then into the heat exchanger 6 in order to heat the fuel 4. The preheated oxidant 31 and the preheated fuel 41 are then brought into contact for oxy-combustion.

FIG. 3 illustrates a variant of the method of FIG. 1 in which the regenerators 11 are in the process of heating the air, enabling hot air to be delivered as combustion air for aero-combustion burners and to deliver hot air in order to preheat the reactants of oxy-fuel burners placed either side of the furnace. By this application, it is then possible to make oxy-fuel burners on each side of the furnace operate continuously, independently of the cycles of the regenerators.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

What is claimed is:

1. A combustion method in a furnace having first and second opposed sides, each side being equipped with regenerators, a plurality of oxy-fired burners each one of which is upstream of the regenerators, and a plurality of air-fired burners each one of which is disposed downstream of the oxy-fired burners, said method comprising first and second cycles, wherein:
   the first cycle comprises the steps of:
      recovering heat from combustion flue gases by the regenerators on the first side;
      heating air using the heat recovered by the regenerators on the first side and combusting that heated air with fuel with the air-fired burners on the first side;
      simultaneous with said step of heating air using the heat recovered by the regenerators on the first side and combusting that heated air with fuel with the air-fired burners on the first side, combusting fuel and oxygen-rich oxidant with the oxy-fired burners on each of the first and second sides,
   the fuel and/or the oxygen-rich oxidant combusted with the oxy-fired burners being heated through heat exchangers with the heated air, the heat exchangers separate from the regenerators on the first side; and
   the second cycle comprises the steps of:
      recovering heat from combustion flue gases by the regenerators on the second side;
      heating air using the heat recovered by the regenerators on the second side and combusting that heated air with fuel with the air-fired burners on the second side;
      simultaneous with said step of heating air using the heat recovered by the regenerators on the second side and combusting that heated air with fuel with the air-fired burners on the second side, combusting fuel and oxygen-rich oxidant with the oxy-fired burners on each of the first and second sides, the fuel and/or the oxygen-rich oxidant combusted with the oxy-fired burners being heated through heat exchange with the heated air the heat exchangers separate from the regenerators on the second side.

2. The method of claim 1, wherein the oxygen-rich oxidant has an oxygen concentration greater than 90% by volume.

3. The method of claim 1, wherein the furnace is a glass melting furnace.

4. The method of claim 1, wherein the fuel is heated through heat exchange with the heated air at the heat exchangers.

5. The method of claim 1, wherein the oxygen-rich oxidant is heated through heat exchange with the heated air at the heat exchangers.

6. The method of claim 1, wherein:
   the fuel is heated through heat exchange with the heated air at a first set of heat exchangers; and
   the oxygen-rich oxidant is heated through heat exchange with the heated air at a second set of heat exchangers.

\* \* \* \* \*

UNITED STATES PATENT AND TRADEMARK OFFICE
CERTIFICATE OF CORRECTION

| | |
|---|---|
| PATENT NO. | : 8,851,883 B2 |
| APPLICATION NO. | : 12/064654 |
| DATED | : October 7, 2014 |
| INVENTOR(S) | : Luc Jarry et al. |

Page 1 of 1

It is certified that error appears in the above-identified patent and that said Letters Patent is hereby corrected as shown below:

On the title page

(73) Assignee:

Insert second assignee: --AGC Flat Glas Europe SA, Bruxelles (Watermael-Boitsfort) BE--.

Signed and Sealed this
Eleventh Day of August, 2015

Michelle K. Lee
*Director of the United States Patent and Trademark Office*

UNITED STATES PATENT AND TRADEMARK OFFICE
CERTIFICATE OF CORRECTION

PATENT NO.        : 8,851,883 B2
APPLICATION NO.   : 12/064654
DATED             : October 7, 2014
INVENTOR(S)       : Luc Jarry et al.

It is certified that error appears in the above-identified patent and that said Letters Patent is hereby corrected as shown below:

Title Page,

Item [73], Assignee,

-- ·AGC Flat Glas Europe SA, Bruxelles (Watermael-Boitsfort) --

(as corrected to read in the Certificate of Correction issued August 11, 2015) is deleted and patent is returned to its original state with the assignee name in patent to read -- L'Air Liquide, Societe Anonyme pour l'Etude et l'Exploitation des Procedes Georges Claude, Paris (FR) --.

Signed and Sealed this
Eighth Day of December, 2015

Michelle K. Lee
*Director of the United States Patent and Trademark Office*